(12) United States Patent
Miskie

(10) Patent No.: US 7,143,768 B2
(45) Date of Patent: Dec. 5, 2006

(54) COLLECTION BAG ADAPTED FOR USE IN AN INCONTINENCE MANAGEMENT SYSTEM

(75) Inventor: Mark Miskie, Charlotte, NC (US)

(73) Assignee: Arcus Medical, LLC, Gastonia, NC (US)

( * ) Notice: Subject to any disclaimer, the term of this patent is extended or adjusted under 35 U.S.C. 154(b) by 0 days.

(21) Appl. No.: 10/983,830

(22) Filed: Nov. 8, 2004

(65) Prior Publication Data

US 2005/0283127 A1 Dec. 22, 2005

Related U.S. Application Data

(63) Continuation of application No. PCT/US03/27060, filed on Aug. 29, 2003.

(51) Int. Cl.
*A61F 11/00* (2006.01)
(52) U.S. Cl. .................. 128/885; 604/346; 604/349; 604/355
(58) Field of Classification Search ............... 128/885; 604/347, 349, 351, 353, 355, 346
See application file for complete search history.

(56) References Cited

U.S. PATENT DOCUMENTS

| | | | |
|---|---|---|---|
| 4,713,067 A | 12/1987 | Rothenberg et al. |
| 4,790,834 A | 12/1988 | Austin |
| 4,846,816 A | 7/1989 | Manfredi |
| 5,478,334 A | 12/1995 | Bernstein |
| 5,618,277 A | 4/1997 | Goulter |
| 5,727,568 A | 3/1998 | Kiser |
| 5,797,890 A | 8/1998 | Goulter et al. |
| 6,223,751 B1 | 5/2001 | Park |
| 6,248,096 B1 | 6/2001 | Dwork et al. |
| 6,565,545 B1 | 5/2003 | Frenche |
| 6,613,027 B1 | 9/2003 | Kulikov |
| 6,679,867 B1 | 1/2004 | Miskie |

Primary Examiner—Henry Bennett
Assistant Examiner—Camtu Nguyen
(74) Attorney, Agent, or Firm—Schwartz Law Firm P.C.

(57) ABSTRACT

A collection bag is adapted for communicating with a male incontinence device designed to cover a portion of the penis. The collection bag includes first and second opposing flexible side walls joined together and forming a fluid container for holding urine. A cylindrical neck is formed with the first and second side walls, and defines a mouth for receiving urine passed through the incontinence device and into the fluid container. The neck includes an internal check valve for controlling urine flow and multiple circumferentially-spaced external indexing pins. The indexing pins secure the fluid container to the incontinence device while locating the check valve in a single operative orientation.

12 Claims, 7 Drawing Sheets

COLLECTION BAG ADAPTED FOR USE IN AN INCONTINENCE MANAGEMENT SYSTEM

TECHNICAL FIELD AND BACKGROUND OF THE INVENTION

This invention relates generally to male incontinence, and more specifically to a novel urine collection bag adapted for use in an improved incontinence management system. The invention resides relatively unnoticed under clothing, and offers greater conveniences and an increased freedom of movement often sacrificed with commercially available male incontinence devices and catheters. Users can wear the invention with confidence and without a feeling of self-consciousness.

Incontinence is a growing problem, particularly in those adults ages 65 and older. Approximately four million males in the United States suffer from varying degrees of incontinence. Common causes for this condition include prostate cancer, pelvic trauma, spinal cord injury, medication side-effects, and resulting effects of certain medical conditions such as Alzheimer's and diabetes. Over $16 billion is spent annually on incontinence related care.

The present invention addresses several disadvantages and limitations of prior art collection bags used in certain existing devices and catheters for managing male incontinence. Specifically, the invention effectively eliminates urine back flow, is quickly and easily applied to the incontinence device, and is conveniently emptied when full. The invention is also applicable for monitoring the amount of urine expelled by patients in bladder training during rehabilitation. While not a cure for male urinary incontinence, the invention is intended to allow for a better quality of life with greater conveniences and fewer problems as compared to present, commercially available and accepted incontinent devices.

SUMMARY OF INVENTION

Therefore, it is an object of the invention to provide a urine collection bag which is especially adapted for use in an incontinence management system.

It is another object of the invention to provide a urine collection bag which can be worn relatively unnoticed under clothing and without a feeling of self-consciousness.

It is another object of the invention to provide a urine collection bag which is especially designed for active male adults suffering from moderate to heavy urinary incontinence.

It is another object of the invention to provide a urine collection bag which is conveniently cleaned and reuseable.

It is another object of the invention to provide a urine collection bag which,

It is another object of the invention to provide a urine collection bag which is relatively inexpensive to manufacture.

It is another object of the invention to provide a urine collection bag which includes means for readily ascertaining the level of urine contained in the bag.

It is another object of the invention to provide a urine collection bag which includes a deodorizing agent.

It is another object of the invention to provide a urine collection bag which attaches to a male incontinence device in a single operative orientation.

It is another object of the invention to provide a urine collection bag which incorporates a permanently attached or removable valve cap.

It is another object of the invention to provide a urine collection bag which effectively eliminates the problem of urine back flow.

These and other objects of the present invention are achieved in the preferred embodiments disclosed below by providing a collection bag adapted for communicating with a male incontinence device designed to cover a portion of the penis. The collection bag includes first and second opposing flexible side walls joined together and forming a fluid container for holding urine. The term "joined" is used broadly herein to mean either two formerly separate flexible walls connected together, or integrally formed by, for example, folding over a wall to define an edge. A cylindrical neck is formed with the first and second side walls, and defines a mouth for receiving urine passed through the incontinence device and into the fluid container. The neck includes an internal check valve for controlling urine flow and multiple circumferentially-spaced external indexing pins. The indexing pins secure the fluid container to the incontinence device while locating the check valve in a single operative orientation.

According to another preferred embodiment of the invention, the fluid container has an asymmetrical shape.

According to another preferred embodiment of the invention, the check valve has a crack pressure of less than 0.05 psi at one-half cubic inch of fluid head.

According to another preferred embodiment of the invention, the check valve has a burst pressure of at least 20 psi.

According to another preferred embodiment of the invention, a plurality of touch fastener tabs are adapted for mating with complementary fasteners located on a garment of a wearer to releasably secure the bag to the garment.

According to another preferred embodiment of the invention, at least one of the opposing side walls is at least semi-transparent such that the level of urine contained in the fluid container is readily ascertainable.

According to another preferred embodiment of the invention, a perforated inlet wall is located adjacent the mouth of the neck.

According to another preferred embodiment of the invention, the check valve includes a pivoted seal adapted to releasably seat against the perforated inlet wall at the mouth of the neck.

According to another preferred embodiment of the invention, the seal is formed of a flexible elastomer.

According to another preferred embodiment of the invention, the check valve further includes a resilient backing attached to the pivoted seal. The backing normally urges the seal into a seated position against the perforated inlet wall. When under a minimum crack pressure, the backing allows pivoting movement of the seal from the seated position to a temporarily unseated position away from the perforated inlet wall.

According to another preferred embodiment of the invention, a horizontal drain tube is located at a base of the fluid container.

According to another preferred embodiment of the invention, a flow control valve is connected to the horizontal drain tube.

According to another preferred embodiment of the invention, the indexing pins are asymmetrically-spaced along a circumference of the neck.

In another embodiment, the invention is an incontinence management system for males. The system includes an elongated receptacle designed to cover a portion of the penis. A collection bag communicates with the receptacle, and includes first and second opposing flexible side walls joined together and forming a fluid container for holding urine. A cylindrical neck is formed with the first and second side walls. The neck defines a mouth for receiving urine passed through the receptacle and into the fluid container. The neck includes an internal check valve for controlling urine flow and multiple circumferentially-spaced external indexing pins. The indexing pins secure the fluid container to the receptacle while locating the check valve in a single operative orientation.

According to another preferred embodiment of the invention, the receptacle includes an outer shell having a reduced-diameter receptacle neck.

According to another preferred embodiment of the invention, the receptacle neck defines a plurality of arcuate, pin-receiving slots adapted for receiving respective indexing pins of the collection bag.

According to another preferred embodiment of the invention, each of the pin-receiving slots extends in a generally j-shaped path having an open starting point and a closed ending point. The collection bag is attached to the receptacle and indexed by aligning the indexing pins with respective starting points, and then twisting the collection bag and receptacle to move the indexing pins from the starting points to the ending points.

According to another preferred embodiment of the invention, a resilient foot is located adjacent the ending point of each pin-receiving slot to snap-attach the collection bag and receptacle together.

BRIEF DESCRIPTION OF THE DRAWINGS

Some of the objects of the invention have been set forth above. Other objects and advantages of the invention will appear as the description proceeds when taken in conjunction with the following drawings, in which.

DESCRIPTION OF THE PREFERRED EMBODIMENT AND BEST MODE

Figure 1:
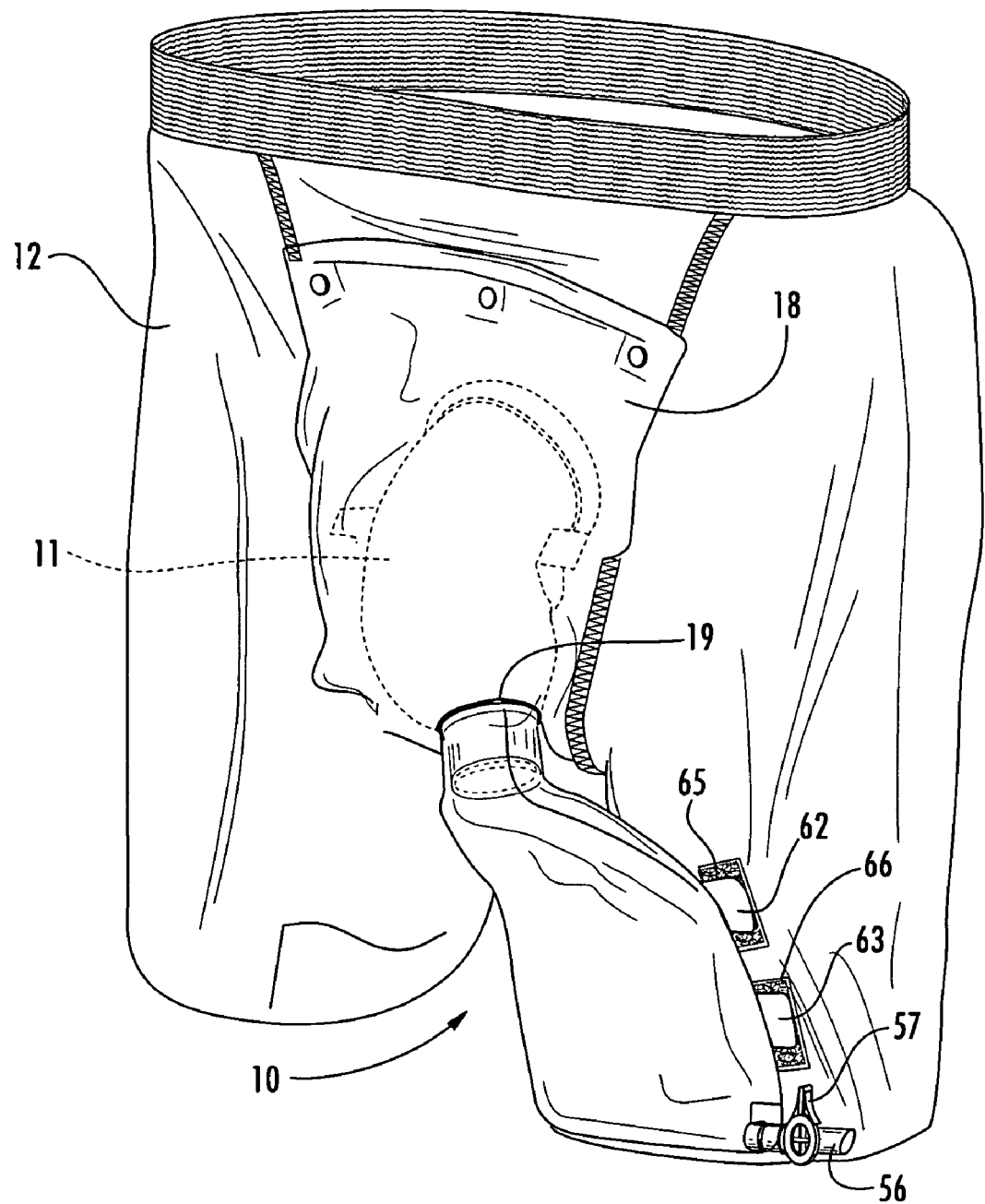
FIG. 1 is a perspective view of an incontinence management system including a urine collection bag according to one preferred embodiment of the present invention.
Figure 2:
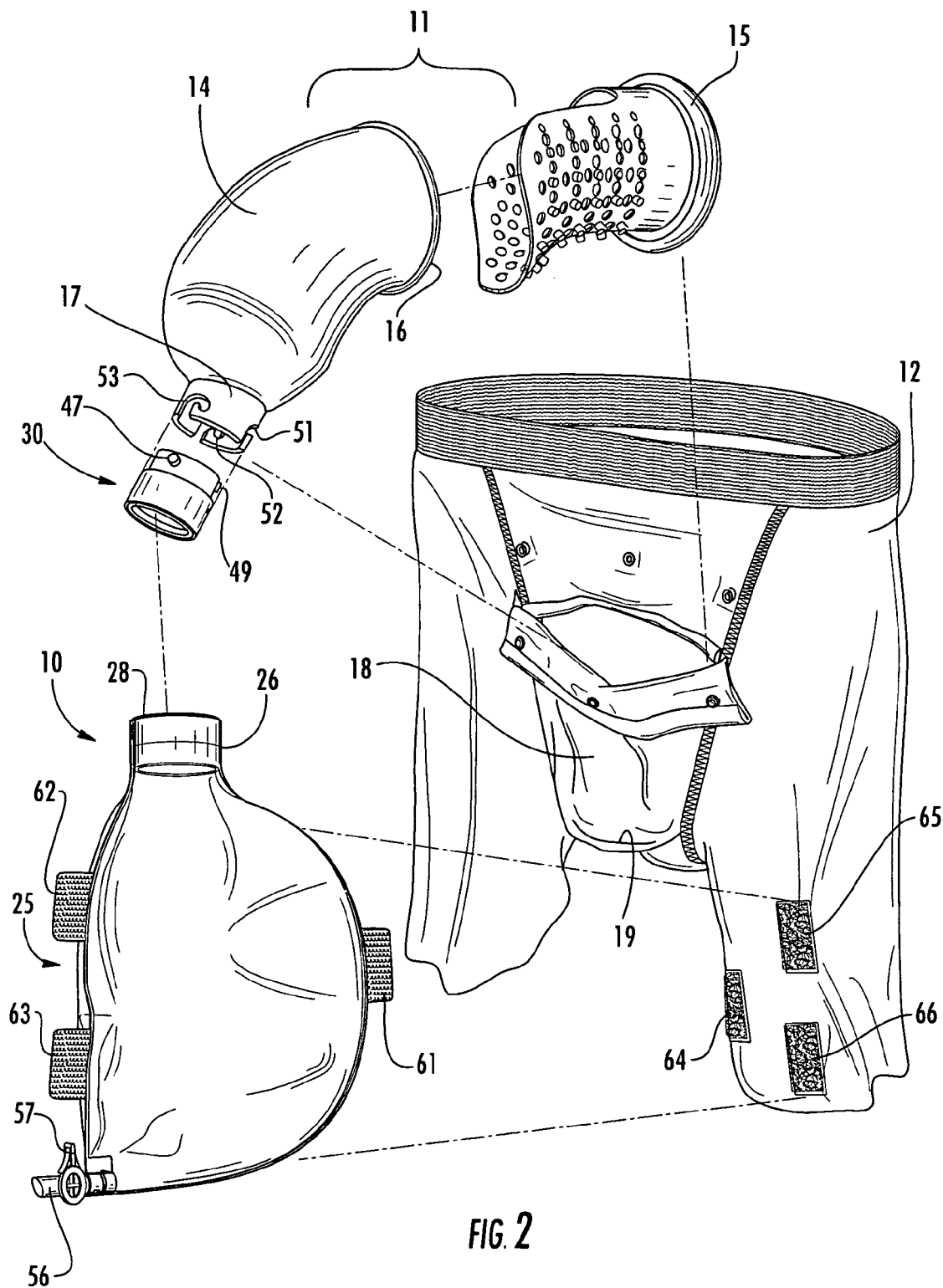
FIG. 2 is a perspective view of the incontinence management system with components of the system exploded away.

Referring now specifically to the drawings, a urine collection bag according to the present invention is illustrated in FIGS. 1 and 2, and shown generally at reference numeral 10. The collection bag 10 is especially applicable for use in an incontinence management system including a multi-piece male receptacle 11 and a supporting undergarment 12. As shown in FIG. 2, the receptacle 11 has an ergonomically-designed, shape-retaining outer shell 14 and a detachable fluid-management insert 15. The fluid-management insert 15 carries the penis of the user inside the receptacle 11 and is detachably received within the outer shell 14. The outer shell 14 has a relatively large diameter open end 16 adapted to receive the penis, and an opposite end defining an elongated reduced-diameter neck 17. The neck 17 is designed to penetrate a crotch panel 18 of the undergarment 12 through a receptacle slit 19. When in use, urine leakage passes outwardly through the receptacle 11 and into the collection bag 10, as described below.

Figure 3:
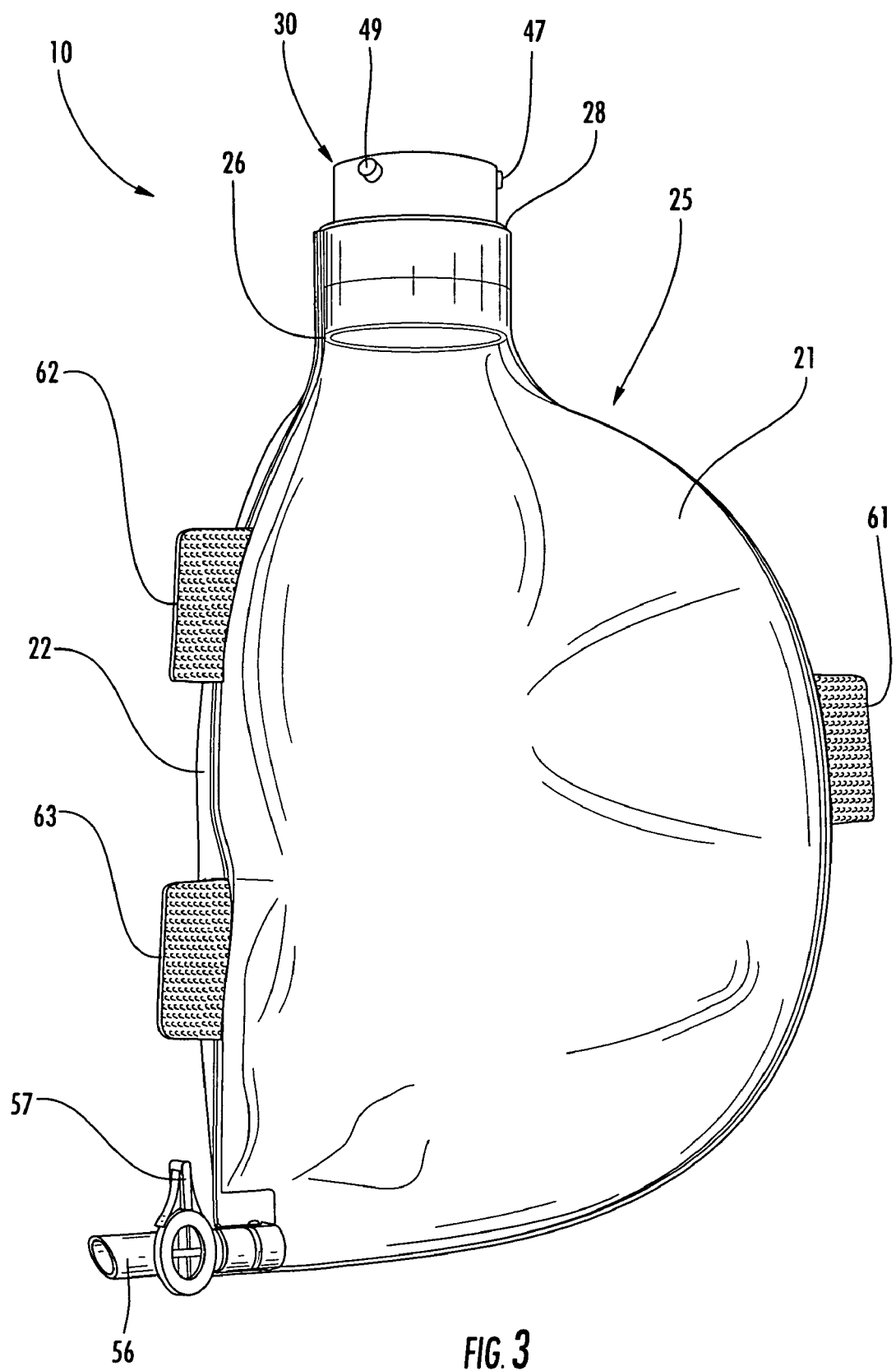
FIG. 3 is an enlarged perspective view of the urine collection bag.

As best shown in FIG. 3, the collection bag 10 is constructed of first and second opposing flexible side walls 21 and 22 joined together and forming a fluid container 25 for holding urine. Preferably, at least one of the side walls 21, 22 is formed of a semi-transparent, white or skin tone polymer which allows the user to visually determine the level of captured urine contained in the fluid container 25. According to one embodiment, the thickness of each side 21, 22 wall is at least 8 mil. The capacity of the fluid container 25 is approximately 500 ml (cc).

Figure 4:
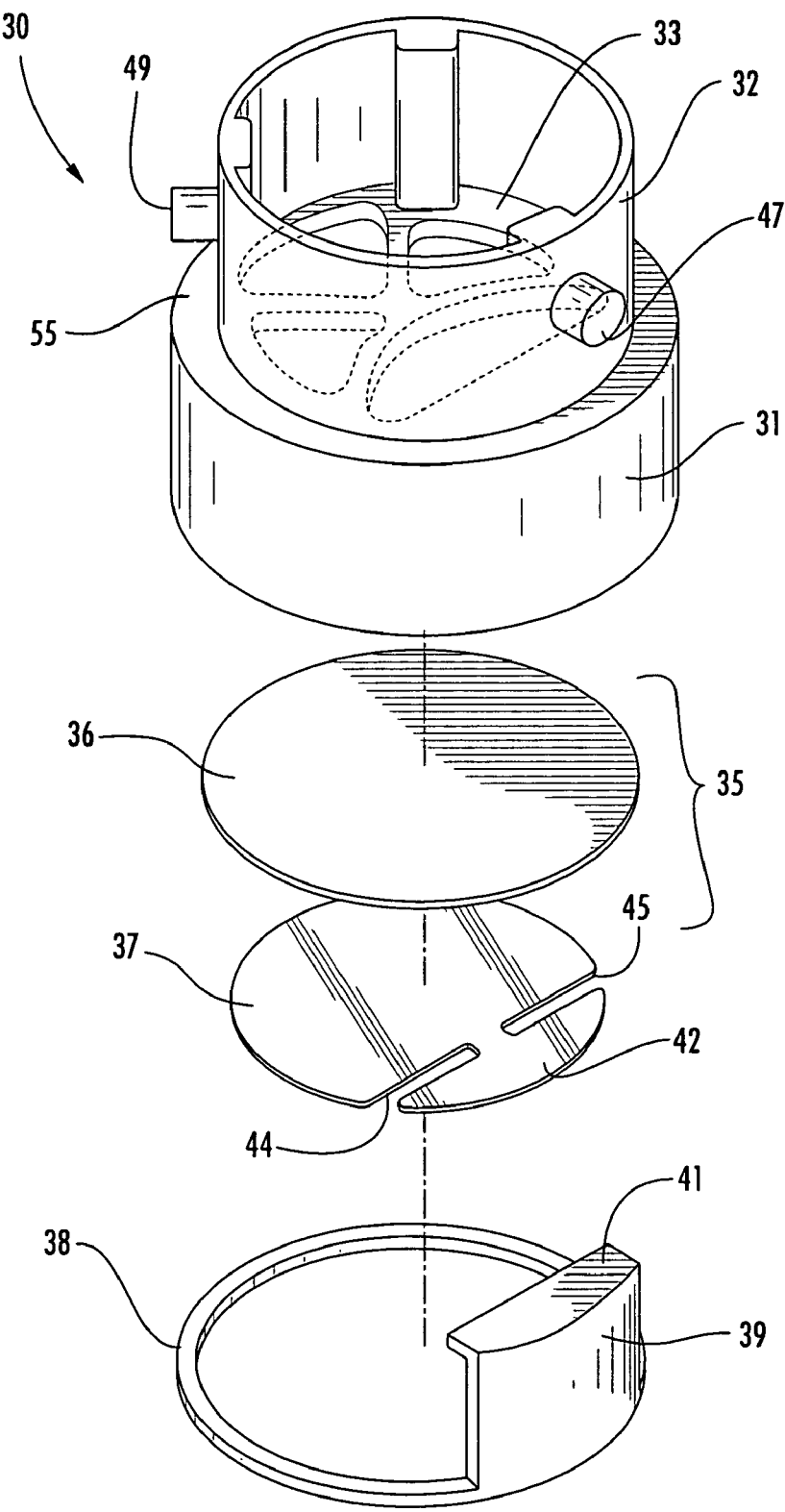
FIG. 4 is an exploded perspective view of the valve cap.

A cylindrical neck 26 is integrally formed with the first and second side walls 21, 22 of the container 25, and defines a mouth 28 for receiving urine passed through the receptacle 11 and into the collection bag 10. In one embodiment, the bag neck 26 includes a separately molded valve cap 30, best shown in FIGS. 3, 4 and 5. The valve cap 30 is located at the mouth 28 of the container 25, and is permanently attached to an interior of the container walls 21, 22 by means, such as gluing or heat welding. The valve cap 30 has an enlarged-diameter cylindrical base 31 received within the fluid container 25 and an integrally-molded cylindrical connecting portion 32 of reduced diameter. A perforated inlet wall 33 is formed between the base 31 and connecting portion 32 of the valve cap 30, and cooperates with a pivoted check valve 35 to control one-way flow of urine outwardly from the receptacle 11 and into the bag 10. The check valve 35 includes a flexible silicone rubber seal 36 and an underlying resilient Mylar® or acetate backing 37 glued together and secured within the cap base 31. The check valve 35 is held in position directly adjacent the inlet wall 33 by a locating ring 38 and support post 39. The support post 39 is permanently glued to the interior of the cap base 31, and has a generally flat landing 41 upon which a fixed portion 42 of the resilient backing 37 is glued. Opposing cut-outs 44 and 45 formed with the backing 37 promote pivoting movement of the check valve 35, and create a biasing spring action which normally urges the silicone seal 36 into a seated position against the perforated inlet wall 33. The perforations formed with the inlet wall 33 are strategically designed and spaced-apart to allow efficient and effective one-way urine flow and proper sealing of the check valve 35.

Figure 5:
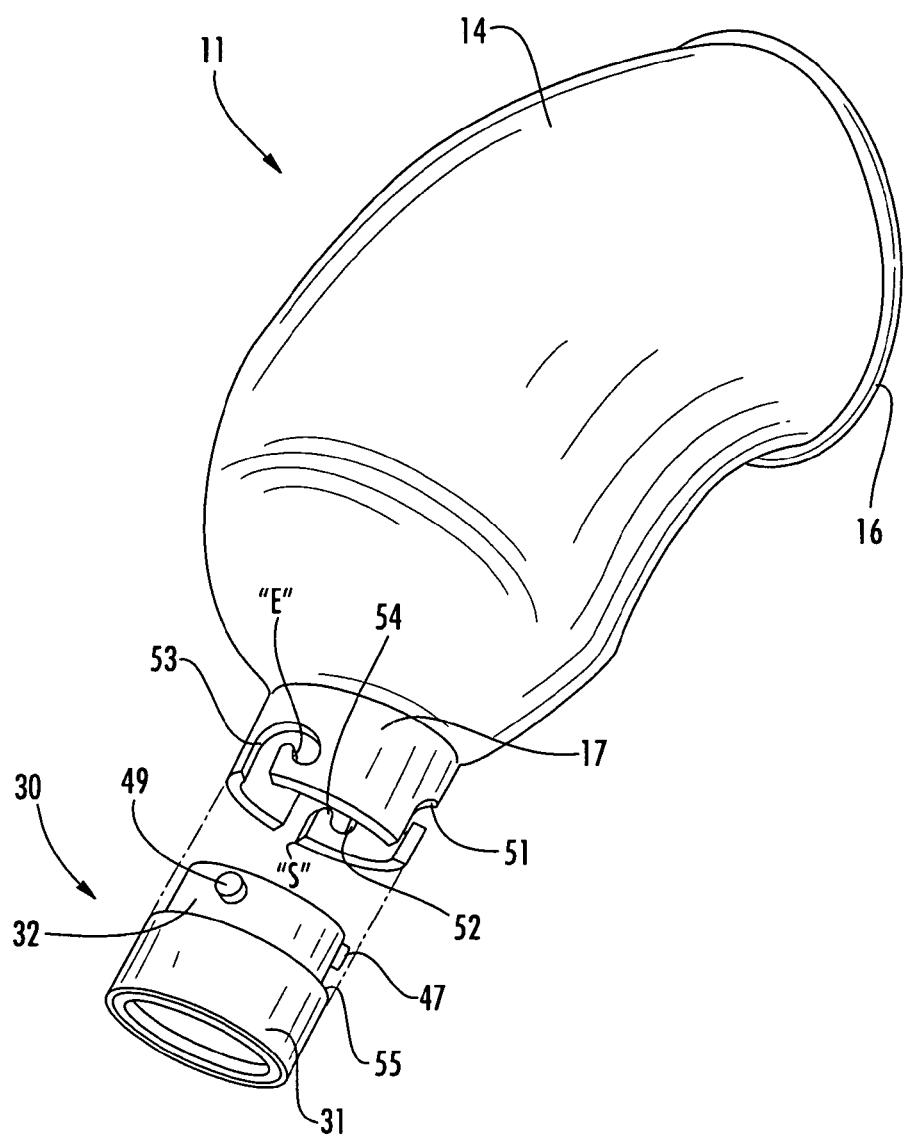
FIG. 5 is an enlarged perspective view of the receptacle and showing alignment of the indexing pins and receptacle slots for indexing the check valve and attaching the bag.

The connecting portion 32 of the valve cap 30 extends outside of the fluid container 25, and has three circumferentially-spaced external indexing pins 47, 48, and 49. As best shown in FIG. 5, the indexing pins 47–49 are adapted to align with respective, generally j-shaped slots 51, 52, and 53 formed-with the neck 17 of the receptacle 11. Each of the slots 51–53 has an open starting point "S" and a closed ending point "E". The receptacle 11 and bag 10 are releasably interconnected by sliding the indexing pins 47–49 through respective starting points "S" of the receptacle slots 51–53 and then twisting slightly to locate the pins 47–49 at respective ending points "E". Preferably, each receptacle slot 51–53 has a projecting resilient foot 54 adjacent its ending point "E" which snap-attaches the indexing pin 47–49 into a frictionally locked position within the slot 51–53. The ending points "E" curve slightly in the direction of the starting points "S" to further strengthen sealing engagement of the receptacle 11 and an annular shoulder 55 formed between the connecting portion 32 and base 31 of the valve cap 30.

Figure 6:
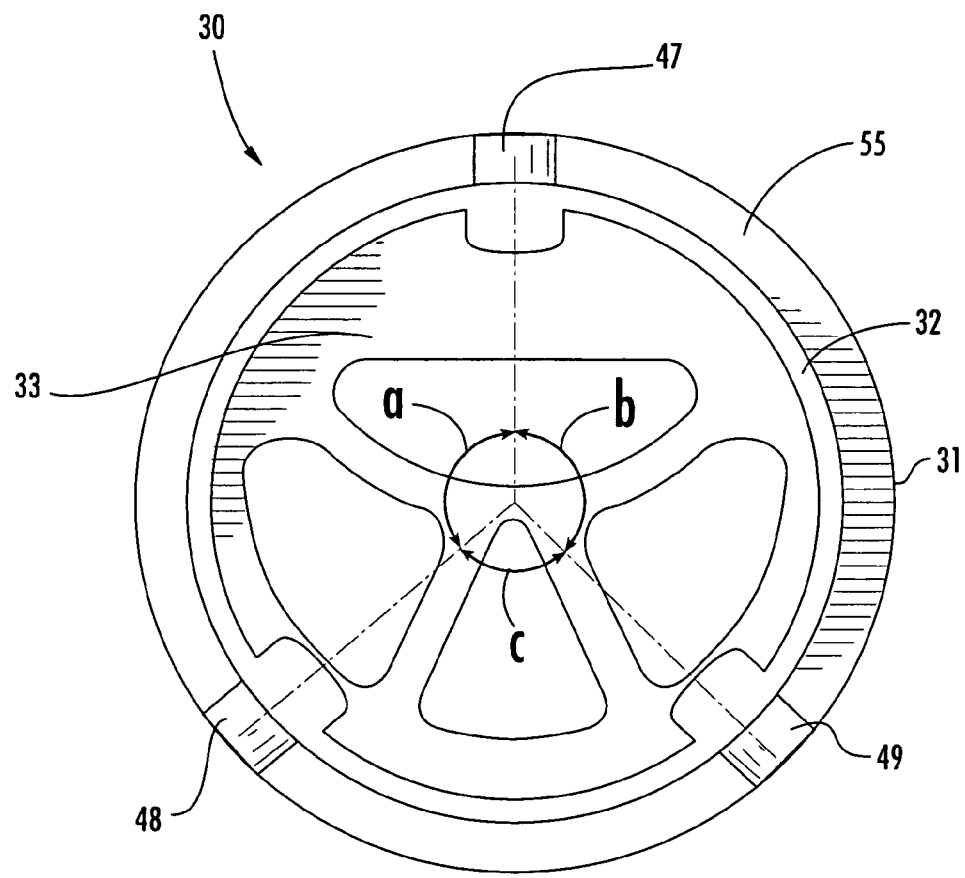
FIG. 6 is a top plan view of the valve cap showing the asymmetrical spacing of the indexing pins.

As best shown in FIG. 6, the indexing pins 47–49 are asymmetrically spaced apart such that upon connection of the bag 10 and receptacle 11, the check valve 35 and bag 10 are necessarily arranged in one single operative orientation relative to the receptacle 11. For example, the angle "a" between pins 47 and 48 is approximately 130 degrees; the angle "b" between pins 47 and 49 is approximately 135 degrees; and the angle "c" between pins 48 and 49 is approximately 95 degrees. Because of this asymmetry, the indexing pins 47–49 align with the slots 51–53 of the receptacle 11 in only one correct manner. As a result, the check valve 35 is designed to open outwardly from the lowest point of urine collection within the neck 17 of the receptacle 11. The circumferential spacing of the indexing pins 47–49 further provides relatively uniform distribution of holding force when the pins 47–49 are received within the slots 51–53 to interconnect the bag 10 and receptacle 11.

Figure 7:
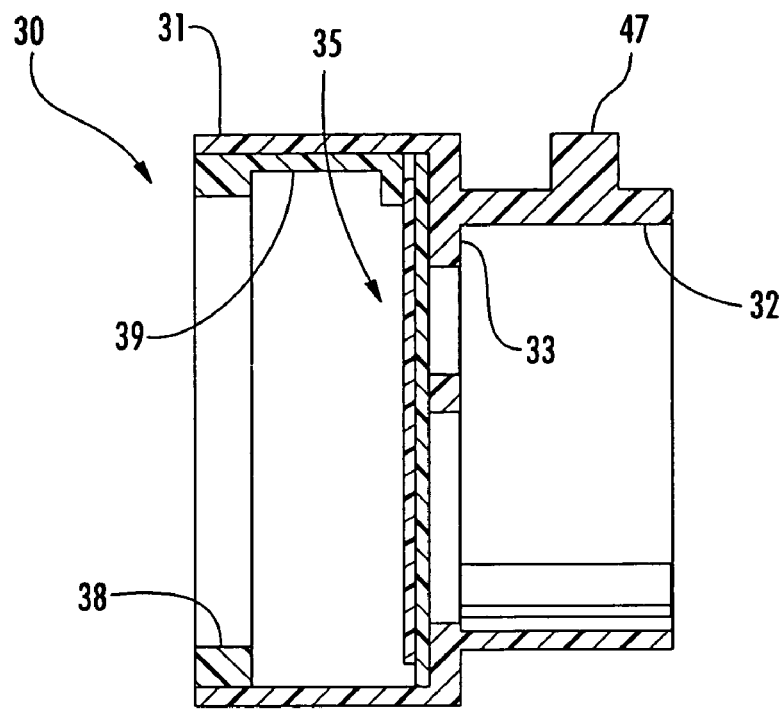
FIG. 7 is a side cross-section of the valve cap with the check valve closed.
Figure 8:
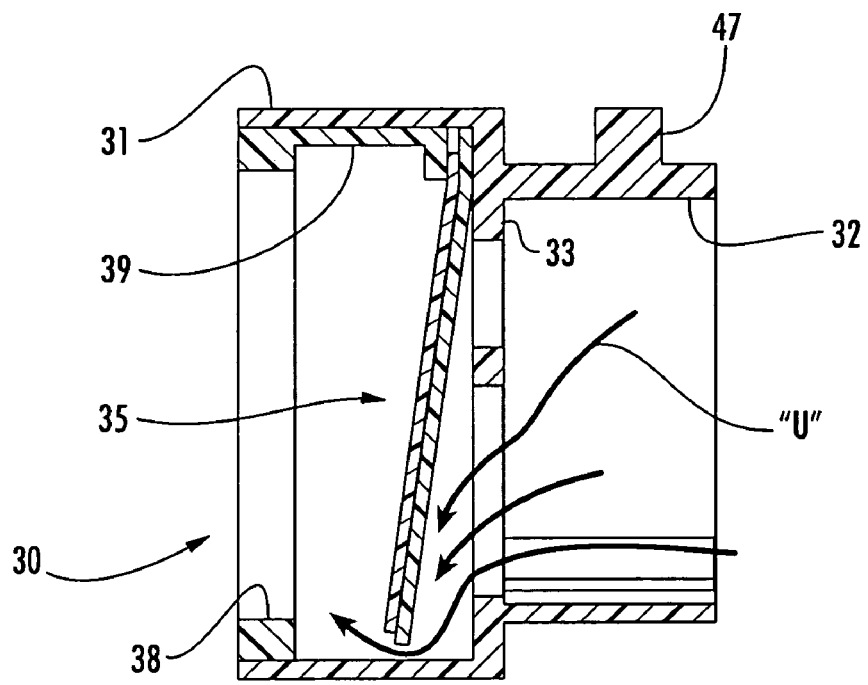
FIG. 8 is a side cross-section of the valve cap with the check valve open.

FIGS. 7 and 8 demonstrate operation of the check valve 35. In a normal condition, the check valve 35 remains closed, as shown in FIG. 7, and prevents any back flow of urine from the fluid container 25 and into the receptacle 11. When leakage occurs, as indicated by direction arrows "U", the check valve 35 temporarily opens to enable urine flow outwardly from the receptacle 11 and into the container 25. When urine flow ceases, the biasing force created by the resilient backing 37 promptly closes the check valve 35 to prevent back flow. Preferably, the check valve 35 has a crack pressure of approximately 0.02 psi at one-half cubic inch of fluid head, and a burst (back flow) pressure of at least 20 psi. The maximum flow rate of urine through the check valve 35 and into the container 25 is at least 30 cc/sec (1 oz/sec). When the fluid container 25 is full, urine is conveniently discharged from the collection bag 10 through a horizontal drain tube 56 including a user-actuated flow control valve 57. For convenient attachment and detachment, the collection bag 10 may have touch fastener tabs 61, 62, and 63 adapted to mate with complementary fasteners pads 64, 65, and 66 located on the undergarment 12.

A urine collection bag for a male incontinence device is described above. Various details of the invention may be changed without departing from its scope. Furthermore, the foregoing description of the preferred embodiment of the invention and best mode for practicing the invention are provided for the purpose of illustration only and not for the purpose of limitation—the invention being defined by the claims.

I claim:

1. A collection bag adapted for communicating with a male incontinence device designed to cover a portion of the penis, said collection bag comprising:

(a) first and second opposing flexible side walls joined together and forming a fluid container for holding urine; and (b) a cylindrical neck adjacent said first and second side walls and defining a mouth for receiving urine passed through the incontinence device and into said fluid container, said neck comprising a perforated inlet wall located adjacent the mouth, an internal check valve residing adjacent said perforated inlet wall for controlling urine flow, and an indexing element adapted for locating said check valve in a single operative orientation.

2. A collection bag according to claim 1, wherein said fluid container has an asymmetrical shape.

3. A collection bag according to claim 1, wherein said check valve has a crack pressure of less than 0.05 psi at one-half cubic inch of fluid head.

4. A collection bag according to claim 1, wherein said check valve has a burst pressure of at least 20 psi.

5. A collection bag according to claim 1, and comprising a plurality of touch fastener tabs adapted for mating with complementary fasteners located on a garment of a wearer to releasably secure said bag to the garment.

6. A collection bag according to claim 1, wherein at least one of said opposing side walls is at least semi-transparent such that the level of urine contained in said fluid container is readily ascertained.

7. A collection bag according to claim 1, wherein said indexing pins are asymmetrically-spaced along a circumference of said neck.

8. A collection bag according to claim 1, wherein said check valve comprises a pivoted seal adapted to releasably seat against the perforated inlet wall at the mouth of said neck.

9. A collection bag according to claim 8, wherein said pivoted seal is formed of a flexible elastomer.

10. A collection bag according to claim 8, wherein said check valve further comprises a resilient backing attached to said pivoted seal and normally urging said seal into a seated position against the perforated inlet wall, and when under a minimum crack pressure, said backing allowing pivoting movement of said seal from the seated position to a temporarily unseated position away from the perforated inlet wall.

11. A collection bag according to claim 1, and comprising a horizontal drain tube located at a base of said fluid container.

12. A collection bag according to claim 11, and comprising a flow control valve connected to said horizontal drain tube.

* * * * *